United States Patent [19]

Kruger

[11] Patent Number: 5,224,596
[45] Date of Patent: Jul. 6, 1993

[54] SYRINGE CARRIER AND RECAPPING SYSTEM

[76] Inventor: Kerry Kruger, 35 Winslow Dr., Winnipeg, Manitoba, Canada, R2M 4M8

[21] Appl. No.: 651,640

[22] Filed: Feb. 6, 1991

[51] Int. Cl.⁵ .................................... B65D 83/10
[52] U.S. Cl. ................................ 206/366; 206/365; 206/460; 206/504; 206/564
[58] Field of Search ............................. 206/364–366, 206/460, 564, 562, 504; 220/23.4

[56] References Cited

U.S. PATENT DOCUMENTS

| | | | |
|---|---|---|---|
| 1,306,591 | 6/1919 | Grant | 206/562 |
| 2,026,396 | 12/1935 | Meinecke | 206/562 |
| 2,048,695 | 7/1936 | Hasenour | 206/562 |
| 2,119,832 | 6/1938 | Schless | 206/562 |
| 2,826,347 | 3/1958 | Schiavo | 206/562 |
| 3,032,186 | 5/1962 | Jenkins | 206/562 |
| 3,145,841 | 8/1964 | McGuire | 206/562 |
| 3,341,053 | 9/1967 | Keene | 206/504 |
| 3,494,201 | 2/1970 | Roach. | |
| 3,862,683 | 1/1975 | Koelichen | 206/504 |
| 4,068,760 | 1/1978 | Johnson, Jr. | 206/562 |
| 4,076,116 | 2/1978 | Sowders | 206/562 |
| 4,658,957 | 4/1987 | Guth et al. | |
| 4,726,466 | 2/1988 | Cooper. | |
| 4,735,617 | 4/1988 | Nelson et al. | |
| 4,836,373 | 6/1989 | Goldman. | |
| 4,850,484 | 7/1989 | Denman. | |
| 4,919,264 | 4/1990 | Shinall. | |
| 4,976,351 | 12/1990 | Mangini et al. | 206/562 |
| 5,007,535 | 4/1991 | Meseke et al. | 206/364 |

Primary Examiner—Paul T. Sewell
Assistant Examiner—Thomas P. Hilliard
Attorney, Agent, or Firm—Adrian D. Battison; Stanley G. Ade; Murray E. Thrift

[57] ABSTRACT

A syringe carrier comprising an elongate member with a plurality of bores thereon for retaining the capped needles of syringes is described. The elongate member is capable of holding a number of syringes and corresponding indicia for each syringe. The syringes are retained within inclined bores on the member, which allows for the easy removal and replacement of the syringe needle, without the need to hold the syringe cap with one's hand. The device can safely carry a number of syringes, as well as allow for the safe removal and insertion of the needle from the syringe cap.

1 Claim, 2 Drawing Sheets

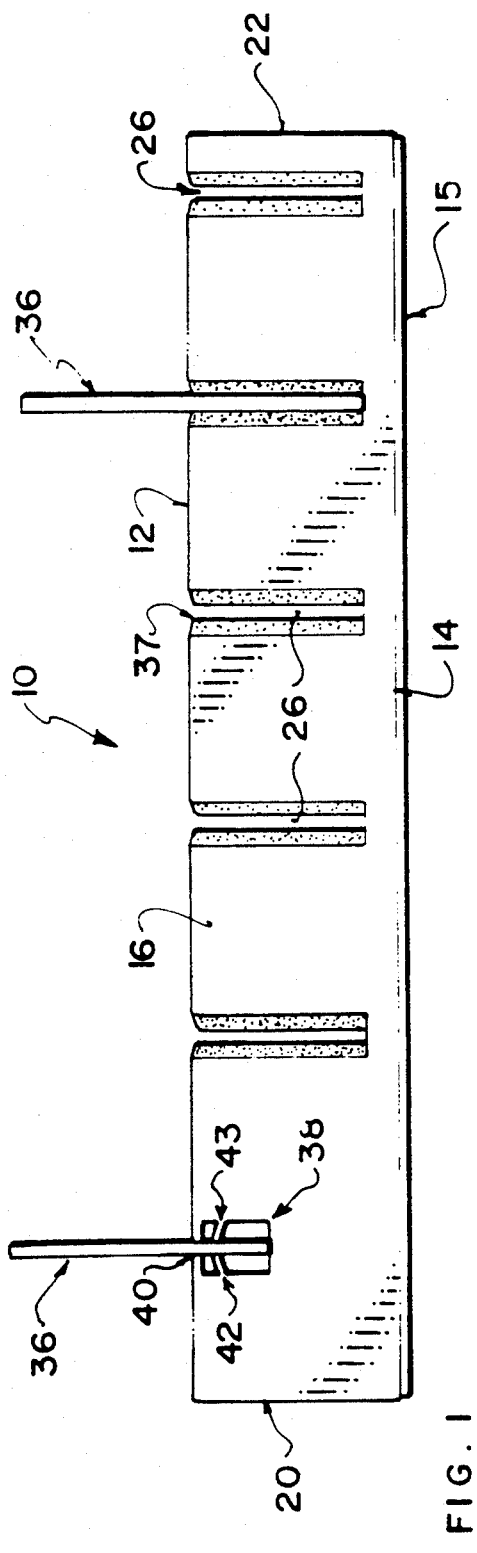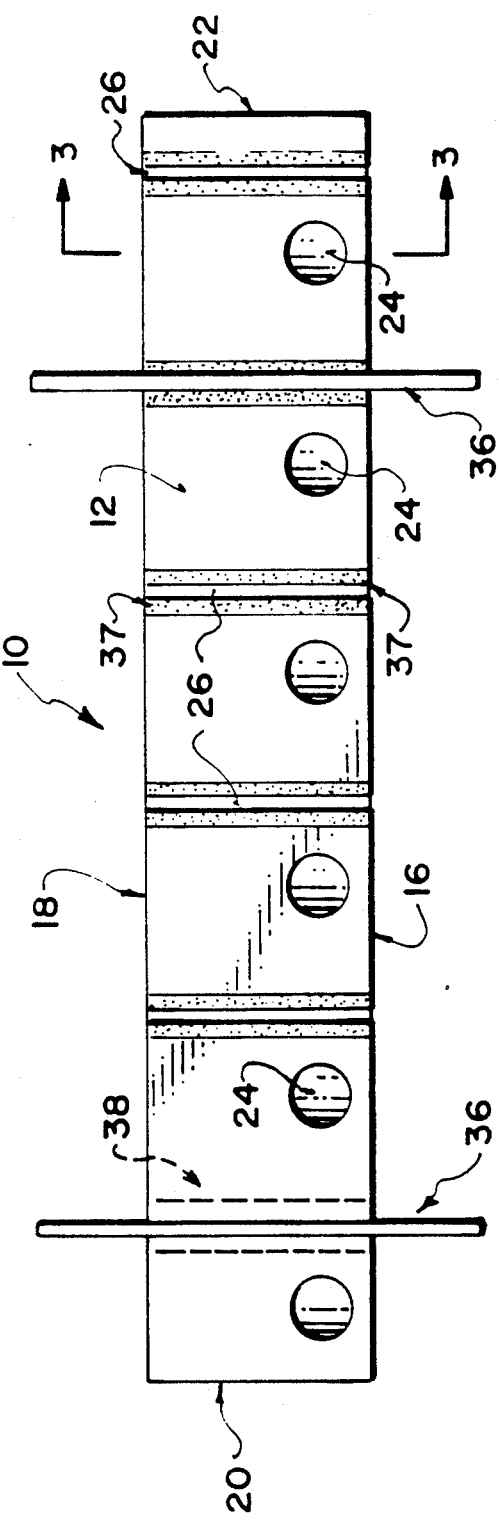

SYRINGE CARRIER AND RECAPPING SYSTEM

FIELD OF THE INVENTION

This invention relates to the field of syringe holders and more particularly, but not exclusively, to a utility tray carrying a safe means for the holding and recapping of hypodermic syringes.

BACKGROUND OF THE INVENTION

Conventional hypodermic syringes carry needles covered by an appropriate end cap or sleeve. In operation, the cap or sleeve is removed before use and put back on after a sample has been taken or treatment administered. Whether administering treatment or taking a sample, the needle may become contaminated by any number of components. An accidental pricking of the user's finger by the needle could result in a very serious virus or bacterial infection.

Most accidents with needles occur when the user is placing the cap on the needle. The needle portion must be carefully inserted back into the cap after use, and a tiny knock or even a distracting noise may cause the user to miss the cap when replacing the needle, thereby causing a puncture or cut on the user's hand that is holding the cap. This, to say the very least, is undesirable as there are many dangerous, if not deadly bacteria and viruses known today.

Guth et al (U.S. Pat. No. 4,658,957) discloses a utility tray that includes a plurality of holders that accomodate removable sleeves or caps from a hypodermic syringe, as well as indicia arranged proximate to the holders to remind the user of the details of the treatment. The trays have compartments in which to store the syringes, alcohol wipes and vials for medication, as well as a waste depository. There is provided a means for holding the syringe caps, as well as a means for holding one syringe, on its side. The syringe is used in conjuction with a series of cap holders, each holding a sleeve portion of a syringe needle. Only one syringe is held on the tray at a time, and this syringe is not attached to a capped needle. This device does not allow for the carrying of a number of syringes, only one at a time, and the syringe is not attached to a needle.

The prior art does not disclose a device that safely carries a number of syringes readily available for use, and corresponding indicia regarding the use of each of the syringes.

SUMMARY OF THE INVENTION

It is an object of the present invention therefore to provide a means for holding a number of syringes, as well as a means to safely carry syringe needles at minimum risk to the operator.

It is a further object of the present invention to also provide a means for holding a number of syringes along with corresponding indicia regarding treatment, as well as a means to safely carry syringe needles at minimum risk to the operator.

The present invention therefore provides a holding device for syringes and associated cards, said device comprising an elongate member, said device having a front and a rear, a top and a bottom, and two ends, said device having a plurality of bores therein, said bores being positioned at spaced locations along the device and extending downwardly into the said device for receiving a cap of a syringe with the syringe projecting upwardly from the member, said device having a plurality of holding means thereon for detachably holding indicia, each holding means being associated with, and adjacent to, a respective bore on the said device.

The present invention further provides a holding device for syringes, said device comprising an elongate member, said device having a front and a rear, a top and a bottom, and two ends, said device having a plurality of bores therein, said bores being positioned at spaced locations along the device and extending downwardly into the said device for receiving a cap of the syringe with the syringe projecting upwardly from the member, said device having adhesive means thereon to attach said device to a surface.

With the foregoing in view, and other advantages as will become apparent to those skilled in the art to which this invention relates as this specification proceeds, the invention is herein described by reference to the accompanying drawings forming a part hereof, which includes a description of the best mode known to the applicant and of the preferred typical embodiment of the principles of the present invention, in which:

DESCRIPTION OF THE DRAWINGS

FIG. 1 is a side view of the preferred embodiment of the present invention.

FIG. 2 is a top view of the preferred embodiment of the present invention.

In the drawings like characters of reference indicate corresponding parts in the different figures.

DETAILED DESCRIPTION

Figure 3:
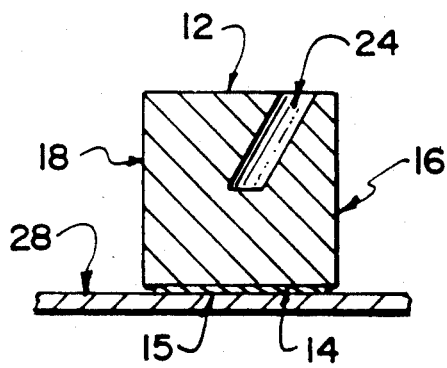
FIG. 3 is a cross sectional side view through 3—3 of FIG. 2.
Figure 4:
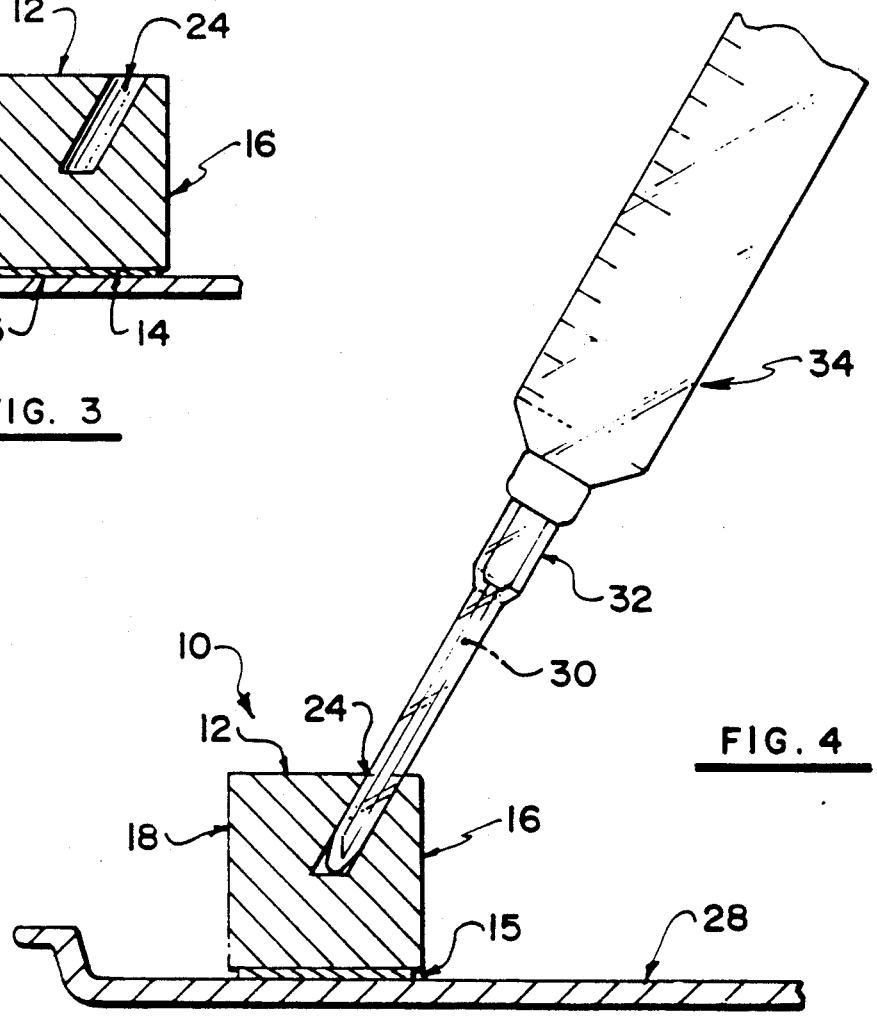
FIG. 4 is a cross sectional side view of the preferred embodiment attached to a tray and holding a capped syringe.

The syringe holding device is shown generally at 10. The elongate device has a top 12, a bottom 14, a front side 16 and a back side 18 between ends 20 and 22. On the top of the device 12 there is a plurality of holes 24. The holes are bored at an inclined angle from a position near the front 16 of the device downwardly and towards the rear of the device. There is adjacent each of the holes 24 a corresponding slot 26 extending from the front side 16 to the back side 18 so that the slot breaks out on the upper surface and at the sides.

On the bottom of the preferred embodiment there is attached thereto a two-sided adhesive 15 that attaches to a utility tray 28. The tray may be of a size of the user's choosing.

In operation, a syringe needle 30, within a syringe cap 32, is fastened to a syringe 34. The covered needle is placed in one of the holes 24 on the device. The result is that the syringe 34 projects outwardly from the front side 16 of the device, preferably towards the user. The slots 26 are immediately adjacent to the holes 24, and in the preferred embodiment there is an equal number of holes 24 and slots 26. Each slot 26 adjacent a hole 24 provides a means for holding a corresponding card 36, upon which all the necessary information regarding treatment to be performed with the syringe in its corresponding hole, is found. To eliminate possible confusion, the holes and slots are arranged in a manner so that an individual hole and slot are obviously corresponding with each other when viewed by the operator. It is also possible to give the corresponding holes and slots identical numbers or markings to enable easy recognition.

The slots 26 may have means thereon to more rigorously retain the card therein, such as a foam lining 37.

As an alternative, the slots 26 may also be defined by an inserted or integrally molded plastic member 38, which has a slot 40 therein to receive a card or a piece of paper regarding the treatment associated with a particular syringe. The slot 40 on the member 38 has two flexible side walls 42 and 43 that frictionally engage and retain the card 36 within the slot 40. With either arrangement, the card is held in place sufficiently to prevent its escape from the slot should the device be tilted or inverted for example if dropped or knocked during carrying.

The syringe sleeve or cap 32 fits within the angled hole 24 and is retained therein. The inclined nature of the holes 24 provide stability for the safe carrying of needles in their sleeves 32 within the holes 24 on the device. The needle and sleeve are held within the hole 24 even when the tray is carried on an angle.

After taking a sample, or administering the treatment, as indicated on the card, the needle is then securely placed back within the sleeve 32 that is in hole 24. The other hand is not necessary to hold the sleeve 32 when replacing the syringe after treatment.

As the treatment may take place in difficult locations, the stable holder and carrier would be very beneficial, as well as safe. One of the most common ways that users of needles poke or infect themselves is by missing the sleeve when attempting to put the needle back into the sleeve. This is potentially very dangerous if working with samples containing dangerous components such as viruses or bacteria. The slots 26 adjacent the holes 24 insure that the corresponding syringes are used for the correct purpose. Accordingly, a number of syringes may be carried on the device, readily available for use as required.

Figure 5:
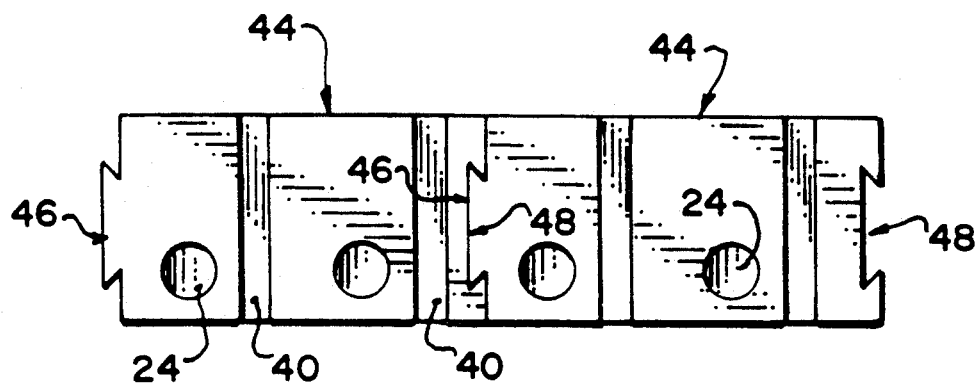
FIG. 5 is a top view of another embodiment of the present invention illustrating interconnecting means.

The device may also be comprised of a number of blocks, that attach to each other to form an elongate syringe holder. The device may also attach to a surface other than a tray. Each block would have a hole and corresponding slot, and means to attach the blocks to each other and the tray or surface. The interconnecting blocks may have thereon any desired number of holes and slots. The blocks may then be assembled to carry the desired number of syringes. One possible means of interconnecting the blocks is illustrated in FIG. 5.

Each block 44 has two holes 24 and two slots 40, along with a connecting member 46 on one end and a receiving slot 48 on the other.

The member 46 slides into the receiving slot 48 and is frictionally held therein. Other connecting means are also possible.

The device may be used for pharmacies as well as the hospital or clinic setting, or by anyone who uses one or more syringes.

Since various modifications can be made in my invention as hereinabove described, and many apparently widely different embodiments of same made within the spirit and scope, it is intended that all matter contained in the accompanying specification shall be interpreted as illustrative only and not in a limiting sense.

I claim:

1. A combination comprising a plurality of syringes each having a needle, a syringe body to which the needle is attached and a needle cap covering the needle and attached to the syringe body, a plurality of information cards, each associated with a respective one of the syringes for carrying information on the card relating to the syringe, and a holder for supporting the plurality of syringes and the plurality of cards, the holder comprising a holder body having an upper surface, two sides and a planar lower surface, adhesive means on the planar lower surface by which the holder body can be mounted on a planar support surface of a tray with the two sides extending generally upwardly from the support surface and the upper surface spaced away from the support surface of the tray, the holder body including for each of said syringes a respective one of a plurality of transporting and recapping systems for the syringes, each transport and recapping system consisting solely of an elongate bore having a smooth cylindrical inner surface, a closed end at one end of the cylindrical surface and an open end at an upper end of the cylindrical surface breaking out on the upper surface, the cylindrical inner surface having a longitudinal axis inclined relative to an imaginary line at right angles to the planar lower surface toward one side of the body, the holder body including for each of the information cards a respective one of a plurality of card holders each card holder comprising a planar slot extending across the holder body and breaking out from the holder body at the upper surface and at the sides of the holder body so as to allow receipt in the slot of an information card having a length greater than a width of the holder body, and friction grasping means mounted in the planar slot and extending toward each surface of the card for engaging each side of the card for holding the card in the slot, the slot being arranged at spaced positions along the length of the holder body each slot being arranged adjacent a respective one of the bores.

* * * * *